(12) United States Patent
Drent et al.

(10) Patent No.: US 7,186,868 B2
(45) Date of Patent: Mar. 6, 2007

(54) HYDROFORMYLATION PROCESS FOR THE CONVERSION OF AN ETHYLENICALLY UNSATURATED COMPOUND TO AN ALCOHOL

(75) Inventors: Eit Drent, Amsterdam (NL); Jacoba Catherina Lucia Johanna Suykerbuyk, Amsterdam (NL)

(73) Assignee: Shell Oil Company, Houston, TX (US)

( * ) Notice: Subject to any disclaimer, the term of this patent is extended or adjusted under 35 U.S.C. 154(b) by 555 days.

(21) Appl. No.: 10/737,498

(22) Filed: Dec. 16, 2003

(65) Prior Publication Data
US 2004/0152928 A1 Aug. 5, 2004

(30) Foreign Application Priority Data
Dec. 17, 2002 (EP) ................... 02258669

(51) Int. Cl.
*C07C 29/44* (2006.01)
*C07C 29/36* (2006.01)
*C07C 29/32* (2006.01)
*C07C 29/16* (2006.01)
*C07C 29/141* (2006.01)

(52) U.S. Cl. .............. 568/909; 568/814; 568/850; 568/876; 568/878; 568/880; 568/881; 568/882

(58) Field of Classification Search ............ 568/850, 568/909, 814, 876, 878, 880, 881, 882
See application file for complete search history.

(56) References Cited

U.S. PATENT DOCUMENTS

| 3,418,351 A | 12/1968 | Greene et al. ............ 260/439 |
| 5,004,823 A | 4/1991 | Devon et al. ............ 556/136 |
| 5,994,591 A | 11/1999 | Arnoldy et al. ............ 568/454 |
| 6,037,506 A | 3/2000 | Bolinger ............ 568/909 |

FOREIGN PATENT DOCUMENTS

| EP | 0273489 A2 | 11/1987 |
| EP | 0350921 A1 | 7/1989 |
| EP | 0 350 921 A1 * | 1/1990 |
| EP | 0489472 A2 | 11/1991 |
| WO | WO 95/05354 | 2/1995 |

OTHER PUBLICATIONS

International Search Report of Apr. 28, 2004.
Notification of Transmittal of the International Preliminary Examination Report for PCT/EP 03/51027 of Apr. 19, 2005.

* cited by examiner

*Primary Examiner*—Elvis O. Price

(57) ABSTRACT

The invention pertains to a hydroformylation process for the conversion of an ethylenically unsaturated compound to an alcohol comprising a first step of reacting at an elevated temperature in a reactor the ethylenically unsaturated compound, carbon monoxide, hydrogen, and a phosphine-containing cobalt hydroformylation catalyst, which are dissolved in a solvent, followed by a second step of separating a mixture comprising the alcohol and heavy ends from a solution comprising the catalyst and the solvent, followed by a third step of recycling the solution to the reactor.

16 Claims, No Drawings

HYDROFORMYLATION PROCESS FOR THE CONVERSION OF AN ETHYLENICALLY UNSATURATED COMPOUND TO AN ALCOHOL

FIELD OF THE INVENTION

The invention relates to a process for the hydroformylation of ethylenically unsaturated compounds by reaction thereof with carbon monoxide and hydrogen in the presence of a catalyst.

BACKGROUND OF THE INVENTION

The hydroformylation of ethylenically unsaturated compounds to form alcohols is of considerable industrial importance. The process has been in commercial operation for decades and over the years much development work has been done to optimize the reaction conditions, the catalyst system, and the equipment. Although significant progress as regards higher yield and selectivity to the desired reaction products has been made, it is felt that in some aspects further improvement of the process is still needed.

Conventional modes of operation are based on the recovery of a cobalt carbonyl hydrocarbyl tert-phosphine complex by use of a recycle solution purge stream, as was disclosed in U.S. Pat. No. 3,418,351. According to such processes the contents of the reactor pass to a stripper where hydrogen, carbon monoxide, and the ethylenically unsaturated compound are vented to a recycle compressor and retuned to the reactor. The alcohol products are taken off overhead of the stripper and the bottom of the stripper is a solution of the catalyst complex and high-boiling byproducts, which are known as heavy ends. The bottom solution is recycled to the reactor, but to prevent build-up of heavy ends, at least a portion of this stream is subjected to a bleeding off process to separate the catalyst complex from the heavy ends. Unfortunately, this bleeding off procedure leads to a substantial loss of active catalyst, which cannot easily be separated completely from the heavy ends. Since the catalyst is the most expensive constituent of the process there is a need for a process preventing such loss of active catalyst complex.

The present invention provides a process that does not lead to substantial loss of catalyst during the recycle process and that prevents the formation of heavy ends as much as possible.

SUMMARY OF THE INVENTION

The present invention therefore pertains to a hydroformylation process for the conversion of an ethylenically unsaturated compound to an alcohol comprising a first step of reacting at an elevated temperature in a reactor the ethylenically unsaturated compound, carbon monoxide, hydrogen, and a phosphine-containing cobalt hydroformylation catalyst, which are dissolved in a solvent, followed by a second step of separating a mixture comprising the alcohol and heavy ends from a solution comprising the catalyst and the solvent, followed by a third step of recycling the solution to the reactor. In a preferred processes according to the invention the phosphine is attached to a non-ionic polar moiety and the solvent is selected to dissolve the catalyst and to form a two-phase liquid system with the alcohol at a lower temperature than the reaction temperature.

DETAILED DESCRIPTION OF THE INVENTION

According to the invention a solvent is used that at the reaction temperature forms a homogeneous single liquid phase with all the reaction components of the hydroformylation reaction, including the ethylenically unsaturated compound, dissolved carbon monoxide, dissolved hydrogen, the phosphine-containing cobalt hydroformylation catalyst, and also the alcohol product that is formed during the reaction. The reaction mixture, however, forms a two-phase liquid system after cooling down to a temperature that is lower than the reaction temperature, for instance at room temperature or preferably higher, with one phase comprising the solvent and the catalyst and the other phase comprising the alcohol product and heavy ends that are formed during hydroformylation reactions. Suitable solvents can easily be found by performing a simple test tube assay, by determining whether a two-phase system is formed with the alcohol at room temperature and whether this system transforms to one-phase system upon heating to the reaction temperature. Suitable solvents may be selected from amide-, imide-, sulfone-, pyrrolidine-, and imidazole-containing solvents, and N-containing aromatic solvents, and mixtures thereof. Most preferred are sulfolane and mixtures comprising sulfolane.

The ethylenically unsaturated compound, used as starting material, is preferably an olefin having from 2 to 100 carbon atoms per molecule, or a mixture thereof. They may comprise one or more double bonds per molecule. Preferred are internal olefins having from 5 to 60 carbon atoms, more preferably 6 to 30 carbon atoms, or mixtures thereof. Such olefin mixtures are commercially readily available, for example the olefin mixtures, obtained as products of a process for the oligomerization of ethylene, followed by a double bond isomerization and disproportionation reaction. In the process of the invention, these internal olefins, usually mixtures of linear internal olefins with 2 to 100 carbon atoms per molecule, or closer boiling fractions of such mixtures, can be hydroformylated at high rates and almost complete conversion. Examples are mixtures of linear internal $C_6$ to $C_8$ olefins, and of linear internal $C_{10}$ to $C_{14}$ olefins.

Substituted olefins may also be used, for example unsaturated carboxylic acids, esters of such acids, or unsaturated esters of carboxylic acids, e.g. allyl acetate, or the corresponding nitriles, amides, or halogenides thereof, and the like.

If desired, branched olefins such as propene trimer or isomeric butene dimers (such as DIMERSOL™ olefin) may be used, but the hydroformylation product will then, of course, contain branched structures as well.

Also, olefinically unsaturated polymeric feedstock, such as atactic polyolefins like "Shube's mixture" (a mixture of oligomers of $C_{16}$-olefins) may be converted into interesting alcohols (as intermediates to synthetic lubricants, functionalized additives, etc.).

Further, alpha-olefins, such as 1-octene and propene, and diolefins, such as norbornadiene, dicyclopentadiene, 1,5-hexadiene and 1,7-octadiene may be used. The diolefins will of course yield (predominantly) a di-hydroformylated product, although also mono-hydroformylated products may be formed.

Carbon monoxide and hydrogen may be supplied in equimolar or non-equimolar ratios, e.g. in a ratio within the range of about 5:1 to about 1:5, typically about 3:1 to about 1:3. Preferably, they are supplied in a ratio within the range of about 2:1 to about 1:2.

The hydroformylation reaction can be suitably carried out at moderate reaction conditions. The term "elevated temperature" as used throughout the description means any temperature higher than room temperature. Temperatures in the range of about 50 to about 200° C. are recommended, preferred temperatures being in the range of about 70 to about 160° C. Reaction pressures in the range of about 5 to about 100 bar are preferred. Lower or higher pressures may be selected, but are not considered particularly advantageous. Moreover, higher pressures require special equipment provisions.

Preferably, the process is carried out in the presence of a phosphine-containing cobalt hydroformylation catalyst having the formula Co-L, in which L is a ligand that stands for $R_1R_2$—P-A-B wherein $R_1$ and $R_2$ are independently a hydrocarbyl group with $C_1$–$C_{12}$ carbon atoms or together with phosphorus atom P form a cyclic hydrocarbyl moiety with $C_6$–$C_{20}$ carbon atoms which may be substituted, and A-B is a group with a non-ionic polar moiety comprising an apolar spacer A with the formula $C_nH_{2n}$ wherein n is 1 to 12 or cyclic $C_nH_{2n-2}$ wherein n is 6–12, or aromatic $C_nH_{n-2}$, wherein one or more carbon atoms may be replaced by N, O, and/or C=O; and a polar moiety B.

In the organic bridging group, represented by $R_1R_2$, preferably all bridging groups are carbon atoms. Preferably, $R_1$ and $R_2$ together with phosphorus atom P form a cyclic hydrocarbyl moiety. The bivalent (optionally substituted) cyclic group, represented by $R_1$ together with $R_2$, in general comprises at least 5 ring atoms and preferably contains from 6 to 9 ring atoms. More preferably, the cyclic group contains 8 ring atoms. Substituents, if any, are usually alkyl groups having from 1 to 4 carbon atoms. As a rule, all ring atoms are carbon atoms, but bivalent cyclic groups containing one or two heteroatoms in the ring, such as oxygen or nitrogen, atoms are not precluded. Examples of suitable bivalent cyclic groups are 1,4-cyclohexylene, 1,4-cycloheptylene, 1,3-cycloheptylene, 1,2-cyclo-octylene, 1,3-cyclooctylene, 1,4-cyclooctylene, 1,5-cyclooctylene, 2-methyl-1,5-cyclooctylene, 2,6-dimethyl-1,4-cyclooctylene, 2,6-dimethyl-1,5-cyclooctylene groups, and limonenylene. $R_1$ and $R_2$ may also be independently alkyl groups such as ethyl, isopropyl, sec-butyl, and tert-butyl groups, cycloalkyl groups such as cyclopentyl and cyclohexyl groups, aryl groups such as phenyl and tolyl groups, and $R_1$ and $R_2$ may be bivalent groups such as a hexamethylene group.

Preferred bivalent cyclic groups are selected from 1,4-cyclooctylene, 1,5-cyclooctylene, and methyl (di)substituted derivatives thereof.

Mixtures of ligands comprising different bivalent cyclic groups may be used as well, e.g. mixtures of ligands with 1,4-cyclooctylene and ligands with 1,5-cyclooctylene groups.

A-B is a group with a non-ionic polar moiety comprising an apolar spacer A. The nature of A is not essential to the catalytic activity and may be any alkylene, cycloalkylene, or aryl spacer. The spacer may be substituted or may contain heteroatoms, carbonyl groups, and the like. Preferred spacers are $C_nH_{2n}$ wherein n is 1 to 12 or cyclic $C_nH_{2n-2}$ wherein n is 6–12, or aromatic $C_nH_{n-2}$, wherein one or more carbon atoms may be replaced by N, O, and/or C=O.

B can be any polar non-ionic group. Preferred B comprises an amide or imide group, preferably a phthalimide group. Most preferred is a ligand with the structure:

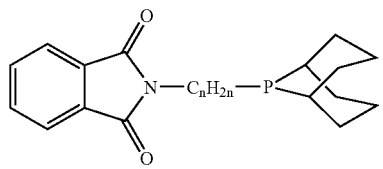

wherein n is 1–3. This ligand is a novel compound for which protection is also sought.

These ligands can be prepared by methods well known in the art. For instance, an organic bromide or iodide B-A-Hal, wherein A and B have the previously given meanings and Hal stands for bromine or iodine, can be reacted with the phosphine H—$PR_1R_2$, wherein $R_1$ and $R_2$ have the previously given meanings, to $R_1R_2$—P-A-B.

As a non-limitative example the following phthalimide ligands with n=1, 2, or 3 were prepared:

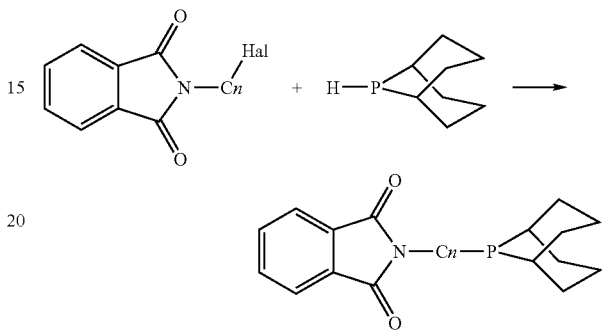

The obtained HBr salts (for Hal is Br) were washed with acetone, neutralized with base in water, and extracted with toluene. The overall product yields were about 50%.

Similarly, pyrrolidine and benzamide derivates were synthesized from the pyrrolidine alcohol and benzamide derivatives, respectively, for instance:

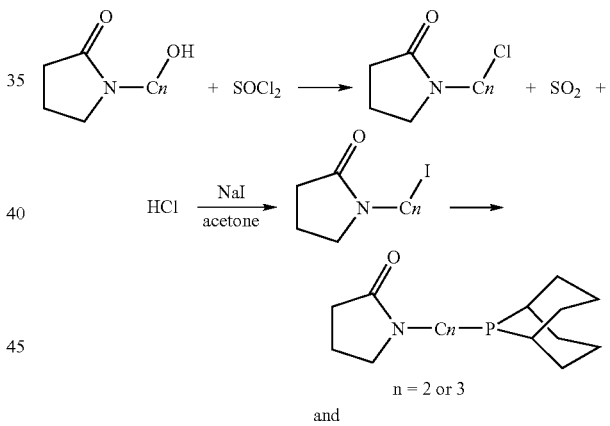

n = 2 or 3
and

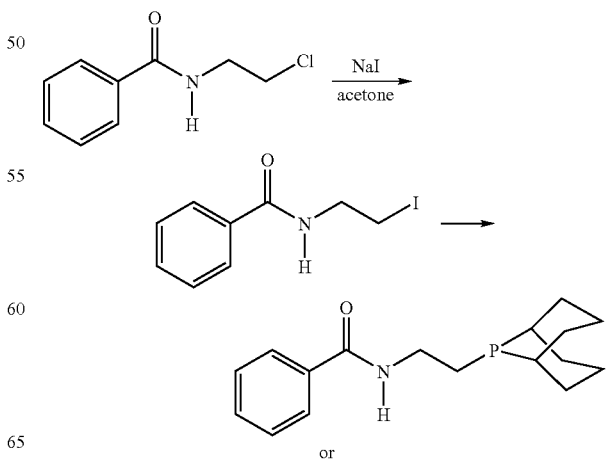

or

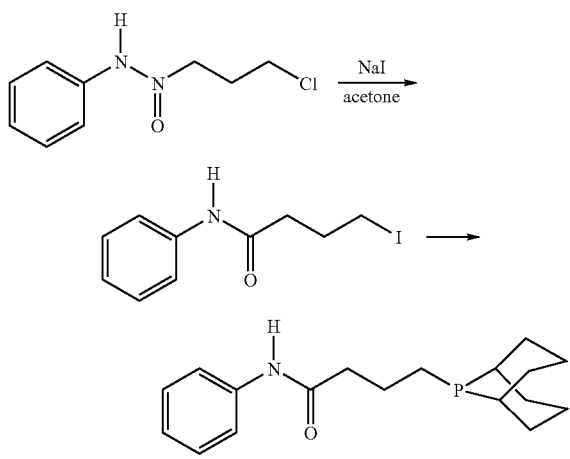

The quantities in which the catalyst system are used, are not critical and may vary within wide limits. Usually amounts in the range of about $10^{-8}$ to about $10^{-1}$, preferably in the range of about $10^{-7}$ to about $10^{-2}$ mole atom of cobalt group metal per mole of ethylenically unsaturated compound are used. The amounts of the participants in the catalyst system are conveniently selected such that per mole atom of cobalt group metal from about 0.5 to about 6, preferably from about 1 to about 3 moles of bidentate ligand are used.

The amount of solvent to be used in the process of the invention may vary considerably. It is within the reach of those skilled in the art to establish in each case the optimal amount of solvent required for dissolving the catalyst and the formation of a two-phase liquid reaction medium. The experimental results provided hereinafter, are also indicative of the amount of solvent, preferably to be used.

The process of the invention is eminently suitable to be used for the preparation of alcohols from internal olefins at high rate, in particular by using a catalyst system as defined above, based on cobalt.

The invention will be illustrated by the non-limiting examples, as described hereinafter.

EXAMPLES

In a 250 ml Hasteloy C autoclave a solution of 0.5 mmole of dicobalt octacarbonyl ($Co_2(CO)_8$) and 1.5 mmole of ligand L (see Table) in 5 ml of 2-ethylhexanol (EHA) was added to a solution of 20 ml of $C_{11}/C_{12}$ SHOP (Shell Higher Olefin Process) alkenes, 10 ml of sulfolane and 25 ml of EHA. The autoclave was closed, flushed twice with 50 bar of nitrogen, and subsequently 20 bar of CO and 40 bar of $H_2$ were added. The autoclave was heated to 160° C. and kept at this temperature for 7 hours. The autoclave was cooled to room temperature and depressurized. The products were analyzed with GC techniques and cobalt analyses were performed on both the sulfolane and alcohol/heavy products layers, using Atomic Absorption Spectroscopy (AAS) on a Perkin Elmer 3100 equipped with a Varian Techtron mercury hollow cathode lamp, operating at 252.1 nm and using an acetylene/oxygen flame. Samples were diluted with methanol and quantitatively analyzed with a calibration curve.

The following results were obtained:

TABLE

| Ligand | Products | | Co in layer (% of total Co) | |
| --- | --- | --- | --- | --- |
| | Heavy ends (%) | Alcohols (%) | Alcohol layer | Sulfolane layer |
| 1 | 5 | 94 | 35 | 65 |
| 2 | 10 | 89 | 18 | 82 |
| 3 | 7 | 92 | 10 | 90 |
| 4 (comparative) | 5 | 93 | 70 | 30* |

*Co plating observed
Ligand 1 = cyclo-octyl=P—$CH_2$—$CH_2$-2-pyrrolidone
Ligand 2 = cyclo-octyl=P—$CH_2$—$CH_2$—N-phthalimide
Ligand 3 = cyclo-octyl=P—$CH_2$—$CH_2$—N-benzamide
Ligand 4 = cyclo-octyl=P—$C_{20}H_{42}$ (ligand according to the prior art)

It can thus be concluded that with the ligands of the invention at similar alcohol production and heavy ends byproduct yields, substantially greater amounts of catalyst remain in the solvent rather than in the product layer, in comparison with the prior art ligand.

Synthetic Examples

General

All reactions with air sensitive compounds or intermediates were carried out in an atmosphere of nitrogen, using Schlenk techniques. All starting materials were commercially available, and were used without drying unless mentioned otherwise.

The starting products 9-phosphabicyclo[3.3.1]nonane and 9-phosphabicyclo[4.2.1]nonane (SH/AH5) were purchased from Cytec as a solution of a 2:1 (SH/AH5) mixture of isomers in toluene (1).

Example 1

Synthesis of 1-(9-phosphacyclononyl)-3-N-pyrimidylpropane (2) (ligand 2)

A mixture of 13.4 g of N-(3-bromopropyl)phtalimide (50 mmole), 15 ml of (1) (60 mmole) and 150 ml of degassed acetonitrile, which formed a white suspension, was heated under reflux for 12 hours. During heating the suspension became clear, and slowly a precipitate of the HBr salt of (2) was formed. The suspension was filtrated over a glass frit, and washed three times with acetone (PA) to remove excess (1). The salt was transferred to an Erlenmeyer and dissolved in about 100 ml of demi-water, after which the HBr salt was neutralized with $NH_4OH$, using phenolphthalein as indicator. The white precipitate was extracted two times with 30 ml of toluene. The combined organic layers were washed with water, dried over $Na_2SO_4$ and concentrated in vacuo. The product was crystallized from toluene/methanol, and the white solid (9.3 g, 56% yield) was identified as pure (2).

Example 2

Synthesis of 1-(2-chloroethyl)-2-pyrrolidinone (3) (ligand 1)

15 ml of thionyl chloride (201 mmole) were kept at 10° C. and stirred, and 20 ml of 1-(2-hydroxyethyl)-2-pyrrolidinone (177 mmole) was added over two hours. A very viscous white suspension was formed, which was heated to 25° C. The mixture was stirred for two hours at 25° C., after which it was heated to 65° C. and stirred under vacuum (125 mbar) to remove $SO_2$ formed and unreacted thionyl chloride. The suspension turned brown during heating. The suspension was neutralized with 1 M $NaOH/H_2O$, and (3) was extracted three times with 30 ml of ether. The combined organic layers were washed with water, dried over $Na_2SO_4$ and concentrated in vacuo. A white powder resulted (21.2 g, 81% yield), which was identified with $^1$H-NMR as pure (3) (9.3 g, 56% yield)

Example 3

Synthesis of 1-(2-iodoethyl)-2-pyrrolidinone (4)

A saturated solution of 15 g of NaI (100 mmole) in approximately 100 ml of acetone (PA) was prepared, and added to 13.9 g of (3) (94 mmole). The resulting well-stirred solution was heated under reflux for 30 minutes. A NaCl precipitate formed, which was filtrated. The filtrate was evaporated in vacuo, and a yellow powder sublimed during the process. This resulted in incomplete drying, which prevented exact yield determination. $^1$H-NMR analysis showed that (4) of more than 90% purity was formed.

Example 4

Synthesis of 1-(9-phosphacyclononyl)-2-N-pyrrolidonethane (5)

A well-stirred mixture of (4) (about 90 mmole in about 10 ml of acetone), 30 ml of (1) (120 mmole) and 150 ml of degassed acetonitrile, which formed a white suspension, was heated under reflux for 12 hours. During heating the suspension became clear, and slowly a precipitate of the HI salt of (5) was formed. The suspension was filtrated over a glass frit, and washed three times with acetone (PA) to remove excess of (1). This procedure was repeated, because much salt precipitated after filtration. A sample of the salt was analyzed with $^1$H- and $^{31}$P-NMR, and identified as HI salt of (5). The salt was transferred to a well-stirred Erlenmeyer and dissolved in about 100 ml of demi-water, after which the Hi salt was neutralized with $NH_4OH$, using phenolphthalein as indicator. The white precipitate was extracted two times with 30 ml of toluene. The combined organic layers were washed with water, dried over $Na_2SO_4$ and concentrated in vacuo. The product was crystallized from toluene/methanol, and the white solid (9.2 g, 40% yield) was identified with $^1$H- and $^{31}$P-NMR analysis as 95% pure (5) (5% oxide).

Example 5

Synthesis of N-(2-iodoethyl)-benzamide (6)

A saturated solution of 15 g of NaI (100 mmole) in approximately 100 ml of acetone (PA) was prepared, and added to 18.2 g of N-(2-chloroethyl)-benzamide (100 mmole). The resulting well-stirred solution first turned blue, but within one minute turned bright yellow, and was heated under reflux overnight. $^1$H-NMR analysis was performed, which showed more than 80% conversion to (6). A NaCl precipitate formed, which was filtrated. The filtrate was evaporated in vacuo, and a yellow powder sublimed during the process. This resulted in incomplete drying, which prevented exact yield determination. $^1$H-NMR analysis showed that (6) of more than 90% purity was formed.

Example 6

Synthesis of N-(2-(9-phosphacyclononyl)-ethyl)-benzamide (7)

A well-stirred mixture of (6) (about 75 mmole in 30 ml acetone), 30 ml of (1) (120 mmole) and 100 ml of degassed acetonitrile, which formed a white suspension, was heated under reflux for 16 hours. All solvents were evaporated with an $N_2$-flow, and a very viscous yellow-brown mixture was obtained. To improve handling, the mixture was diluted with 20 ml of n-hexane, and subsequently extracted three times with 80 ml of hot water. $^{13}$C- and $^{31}$P-NMR-analysis of the extract showed the presence of the Hl salt of (7). The combined water layers were washed with 20 ml of n-hexane and the salt was neutralized with $NH_4OH$, using phenolphthalein as indicator. The resulting very viscous white droplets were extracted two times with a mixture of ether and toluene. The combined organic layers were washed with water, dried over $Na_2SO_4$ and concentrated in vacuo. The resulting very viscous turbid white liquid was analyzed with $^1$H-, $^{13}$C- and $^{31}$P-NMR, after which became clear that a 1:1 (mole/mole) mixture of unoxidized (7) and toluene was formed. After correction, a yield of 18.4 mmole (24.5%) was calculated.

Example 7

Synthesis of N-(3-chloropropyl)-2-pyrrolidone (8)

8.5 ml of thionyl chloride (115 mmole) were kept at 10° C. and stirred, and 10 ml of N-(3-hydroxypropyl)-2-pyrrolidone (70 mmole) were added over 1.5 hours. A very viscous white suspension was formed, which was heated to 25° C. The mixture was stirred for 20 minutes at 25° C., after which it was heated to 65° C. to remove $SO_2$ formed and unreacted thionyl chloride. The suspension was neutralized with 1 M $NaOH/H_2O$, and (8) was extracted three times with 30 ml of ether. The combined organic layers were washed with water, dried over $Na_2SO_4$ and concentrated in vacuo. A white powder resulted (7.4 g, 65% yield), which was identified with $^1$H-NMR as pure (8).

Example 8

Synthesis of N-(3-iodopropyl)-2-pyrrolidone (9)

A saturated solution of 7.5 g of NaI (50 mmole) in approximately 50 ml of acetone (PA) was prepared, and added to 7.4 g of (8) (45 mmole). The resulting well-stirred suspension was heated under reflux, and because $^1$H-NMR analysis after one hour showed little conversion to (9), it was heated under reflux during the weekend. $^1$H-NMR analysis was performed, which showed more than 80% conversion to (6). An NaCl precipitate formed, which was filtrated. The filtrate was evaporated in vacuo, and a white powder (10 g, 87%) resulted.

Example 9

Synthesis of 1-(9-phosphacyclononyl)-3-N-pyrrolidonpropane (10)

A well-stirred mixture of 10 g of (9) (40 mmole), 15 ml of (1) (60 mmole) and 150 ml of degassed acetonitrile, which formed a white suspension, was heated under reflux for 16 hours. No precipitate was detected, but $^{31}$P-NMR analysis in $CDCl_3$ and $D_2O$ showed that the salt of (10) was present in solution (signal at+12 ppm). Therefore, all solvents were evaporated with an $N_2$ flow, and a very viscous brownish suspension was obtained. To improve handling, the mixture was diluted with 20 ml of n-hexane, and subsequently extracted three times with 60 ml of hot water. The combined water layers were washed with 20 ml of n-hexane and the salt was neutralized with $NH_4OH$, using phenolphthalein as indicator, and extracted three times with ether. The combined organic layers were washed with water, dried over $Na_2SO_4$ and concentrated in vacuo, and a clear yellow liquid (5.1 g, 48%) remained. $^{13}C$- and $^{31}P$-NMR showed that pure (10) was formed.

We claim:

1. A hydroformylation process for the conversion of an ethylenically unsaturated compound to an alcohol comprising a first step of reacting at an elevated temperature in a reactor the ethylenically unsaturated compound, carbon monoxide, hydrogen, and a phosphine-containing cobalt hydroformylation catalyst, which are dissolved in a solvent, followed by a second step of separating a mixture comprising the alcohol and heavy ends from a solution comprising the catalyst and the solvent, followed by a third step of recycling the solution to the reactor, wherein the phosphine of the phosphine-containing cobalt hydroformylation catalyst is attached to a non-ionic polar moiety, and wherein the solvent is able to dissolve the catalyst at a temperature which is lower than the elevated reaction temperature and to form a two-phase liquid system with the alcohol.

2. The process according to claim 1 wherein the phosphine-containing cobalt hydroformylation catalyst has the formula Co-L, in which L is a ligand that stands for $R_1R_2$—P-A-B wherein $R_1$ and $R_2$ are independently a hydrocarbyl group with $C_1$–$C_{12}$ carbon atoms or together with phosphorus atom P form a cyclic hydrocarbyl moiety with $C_6$–$C_{20}$ carbon atoms; which may be substituted, and A-B is a group with a non-ionic polar moiety comprising an a polar spacer A with the formula $C_nH_{2n}$ wherein n is 1 to 12 or cyclic $C_nH_{2n-2}$ wherein n is 6–12, or aromatic $C_nH_{2-n}$, wherein one or more carbon atoms may be replaced by N, O, and/or C=O; and a polar moiety B.

3. The process according to claim 2 wherein $R_1$ and $R_2$ together with phosphorus atom P form a cyclic hydrocarbyl moiety and B comprises an amide or imide group.

4. The process of claim 3 wherein B comprises a phthalimide group.

5. The process according to claim 1 wherein the phosphine-containing cobalt hydroformylation catalyst has a ligand with the structure:

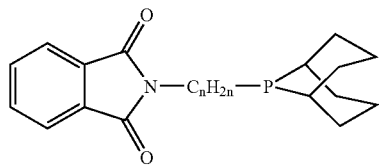

wherein n is 1–3.

6. The process according to claim 1 wherein the first step is performed at a temperature between about 50 and about 200° C. at a pressure of about 5 to about 100 bar.

7. The process according to claim 1 wherein the solvent is selected from the group consisting of an amide, imide, sulfone, pyrrolidine, imidazole, and N-containing aromatic solvents, and mixtures thereof.

8. The process according to claim 7 wherein the solvent is selected from the group consisting of sulfolane and mixtures comprising sulfolane.

9. A hydroformylation process for the conversion of an ethylenically unsaturated compound to an alcohol comprising a first step of reacting at an elevated temperature in a reactor the ethylenically unsaturated compound, carbon monoxide, hydrogen, and a phosphine-containing cobalt hydroformylation catalyst, which are dissolved in a solvent, followed by a second step of separating a mixture comprising the alcohol and heavy ends from a solution comprising the catalyst and the solvent, wherein the phosphine of the phosphine-containing cobalt hydroformylation catalyst is attached to a non-ionic polar moiety, and wherein the solvent is able to dissolve the catalyst at a temperature which is lower than the elevated reaction temperature and to form a two-phase liquid system with the alcohol.

10. The process according to claim 9 wherein the phosphine-containing cobalt hydroformylation catalyst has the formula Co-L, in which L is a ligand that stands for $R_1R_2$—P-A-B wherein $R_1$ and $R_2$ are independently a hydrocarbyl group with $C_1$–$C_{12}$ carbon atoms or together with phosphorus atom P form a cyclic hydrocarbyl moiety with $C_6$–$C_{20}$ carbon atoms; which may be substituted, and A-B is a group with a non-ionic polar moiety comprising an a polar spacer A with the formula $C_nH_{2n}$ wherein n is 1 to 12 or cyclic $C_nH_{2n-2}$ wherein n is 6–12, or aromatic $C_nH_{n-2}$, wherein one or more carbon atoms may be replaced by N, O, and/or C=O; and a polar moiety B.

11. The process according to claim 10 wherein $R_1$ and $R_2$ together with phosphorus atom P form a cyclic hydrocarbyl moiety and B comprises an amide or imide group.

12. The process of claim 11 wherein B comprises a phthalimide group.

13. The process according to claim 9 wherein the phosphine-containing cobalt hydroformylation catalyst has a ligand with the structure:

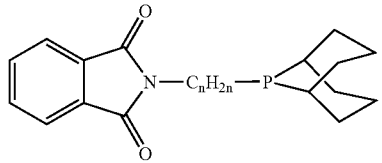

wherein n is 1–3.

14. The process according to claim 9 wherein the first step is performed at a temperature between about 50 and about 200° C. at a pressure of about 5 to about 100 bar.

15. The process according to claim 9 wherein the solvent is selected from the group consisting of an amide, imide, sulfone, pyrrolidine, imidazole, and N-containing aromatic solvents, and mixtures thereof.

16. The process according to claim 15 wherein the solvent is selected from the group consisting of sulfolane and mixtures comprising sulfolane.

* * * * *